United States Patent
Kulesza

(10) Patent No.: US 9,186,310 B2
(45) Date of Patent: Nov. 17, 2015

(54) METHODS AND COMPOSITIONS FOR ALTERATION OF SKIN PIGMENTATION

(76) Inventor: John E. Kulesza, Berlin, CT (US)

( * ) Notice: Subject to any disclaimer, the term of this patent is extended or adjusted under 35 U.S.C. 154(b) by 0 days.

(21) Appl. No.: 14/363,920

(22) PCT Filed: Mar. 16, 2012

(86) PCT No.: PCT/US2012/029456
§ 371 (c)(1),
(2), (4) Date: Aug. 14, 2014

(87) PCT Pub. No.: WO2013/085558
PCT Pub. Date: Jun. 13, 2013

(65) Prior Publication Data
US 2014/0377200 A1  Dec. 25, 2014

Related U.S. Application Data

(60) Provisional application No. 61/568,469, filed on Dec. 8, 2011.

(51) Int. Cl.
| | | |
|---|---|---|
| A61K 8/00 | (2006.01) |
| A61K 8/18 | (2006.01) |
| A61K 8/55 | (2006.01) |
| A61K 31/192 | (2006.01) |
| A61K 31/455 | (2006.01) |
| A61K 31/19 | (2006.01) |
| A61K 31/194 | (2006.01) |
| A61K 31/6615 | (2006.01) |
| A61K 8/362 | (2006.01) |
| A61Q 19/02 | (2006.01) |
| A61K 9/00 | (2006.01) |
| A61K 8/365 | (2006.01) |
| A61K 8/67 | (2006.01) |

(52) U.S. Cl.
CPC . *A61K 8/55* (2013.01); *A61K 8/362* (2013.01); *A61K 8/365* (2013.01); *A61K 8/675* (2013.01); *A61K 9/0014* (2013.01); *A61K 31/19* (2013.01); *A61K 31/192* (2013.01); *A61K 31/194* (2013.01); *A61K 31/455* (2013.01); *A61K 31/6615* (2013.01); *A61Q 19/02* (2013.01); *A61K 2800/592* (2013.01); *A61K 2800/782* (2013.01)

(58) Field of Classification Search
CPC ..... A61K 8/55; A61K 31/192; A61K 31/455; A61K 31/19; A61K 31/194; A61K 31/6615; A61K 8/362; A61K 2800/782; A61K 9/0014; A61K 8/365; A61K 8/675; A61K 2800/592
See application file for complete search history.

(56) References Cited

U.S. PATENT DOCUMENTS

| 7,494,643 | B2 | 2/2009 | Rendon | |
| 2008/0152604 | A1* | 6/2008 | Doering et al. | 424/60 |
| 2009/0110651 | A1 | 4/2009 | Moussou et al. | |
| 2009/0130035 | A1 | 5/2009 | Lange et al. | |
| 2010/0093823 | A1 | 4/2010 | Orlow et al. | |

OTHER PUBLICATIONS

Gillbro J.M., et al., "The Melanogenesis and Mechanisms of Skin-Lightening Agents—Existing and New Approaches," International Journal of Cosmetic Science, 33:210-221, 2011.
International Search Report for PCT/US2012/029456 dated Nov. 29, 2012.

* cited by examiner

*Primary Examiner* — Lezah Roberts
*Assistant Examiner* — Nannette Holloman
(74) *Attorney, Agent, or Firm* — Dinsmore & Shohl LLP; Weston R. Gould

(57) ABSTRACT

Compositions are provided that possess levels of phytic acid and optionally a hydroxy acid and/or azelaic acid that act synergistically with the phytic acid to reduce melanin levels in skin. Improved reduction in melanin levels and hyperpigmentation are achieved at low levels of azelaic acid and phytic acid such that greater comfort and reduced irritation are observed at an administration site. Processes of reducing melanin levels or treating hyperpigmentation are provided by topically administering compositions of the invention.

18 Claims, 3 Drawing Sheets

METHODS AND COMPOSITIONS FOR ALTERATION OF SKIN PIGMENTATION

CROSS REFERENCE TO RELATED APPLICATIONS

This application is the U.S. National Phase application of PCT/US2012/029456, filed Mar. 16, 2012, and depends from and claims priority to U.S. Provisional Application No. 61/568,469, filed Dec. 8, 2011, the entire contents of both of which are incorporated herein by reference.

FIELD OF THE INVENTION

The invention relates to altering the level of pigmentation in the skin. Compositions are provided that provide low levels of active agents that act synergistically to reduce melanin levels in cells, thus providing the ability to reduce the extent of pigmentation in a tissue such as skin with reduced side effects, improved subject compliance, and pleasing results.

BACKGROUND OF THE INVENTION

Melanins serve as the primary skin coloration pigments. In human skin, two primary melanin types are present. The black/brown melanin, eumelanin, provides primary skin coloration with eumelanin more prevalent in humans with dark skin color. Eumelanin is derived from hydroxy-substituted aromatic amino acids such as L-tyrosine and L-DOPA. Eumelanin is believed to include 5,6-dihydroxyindole and 5,6-dihydroxyindole-2-carboxylic acid polymers. The yellow to red pheomelanins are found in humans of both dark and light skin coloration with the greatest quantities found in red hair. Pheomelanins are formed from sulfur-containing molecules and differ from eumelanin in the presence of benzothiazine and benzothiazole units in the oligomers when the amino acid L-cysteine is present.

Melanin is produced in melanocytes found at the dermis-epidermis junction. The melanin is transferred from the melanocytes to keratinocytes that form at this junction and then migrate to the outer epidermal layer transporting the melanin to the skin surface. The resulting coloration of the skin is dependent on the rate of transfer of melanin to keratinocytes, as well as the number, size, and melanin content of the keratinocytes in particular regions of the skin.

Irregular skin pigmentation occurs from the uneven distribution of melanocytes. Hyperpigmentation, or the presence of focused or unfocused skin pigmentation of darker appearance than the surrounding tissue is common. Hyperpigmentation may be the result of pregnancy where women experience a darkening of some regions of the skin often referred to as melasma or the mask of pregnancy. Melasma may also be linked to the use of hormone based birth control or hormone replacement therapy. Many people develop dark spots with age due to sun exposure known as solar lentigenes or liver spots. Other forms of hyperpigmentation may occur as a result of persistent acne, burns, bites or other skin injuries.

It is commonly desirable to reduce or remove these and other types of skin pigmentations. People that present with excessive or unwanted age spots or freckles may wish to have these areas less pronounced relative to surrounding skin tissue. Several compositions have been developed to target such areas. It is all too common, however, for these compositions to either fail to provide the desired effects, or to produce unwanted irritation of the skin that can actually stimulate melanocyte activity paradoxically darkening the skin. Thus, there remains a need for improved compositions and methods for altering skin pigmentation.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Compositions are provided that include azelaic acid, one or more hydroxy acids, or a combination thereof A composition also includes phytic acid. The compositions include the azelaic acid or hydroxy acid, combined and phytic acid at low levels of each that surprisingly act synergistically to reduce melanin content in a subject, or a portion thereof. Processes are also provided whereby a composition is contacted with a subject, or portion thereof, and the level of a melanin is reduced by the contacting.

The compositions and processes provide for unexpectedly efficacious reduction in melanin levels without the risk of unwanted irritation associated with other products with higher levels of an active agent.

DETAILED DESCRIPTION OF EMBODIMENTS OF THE INVENTION

Figure 1:
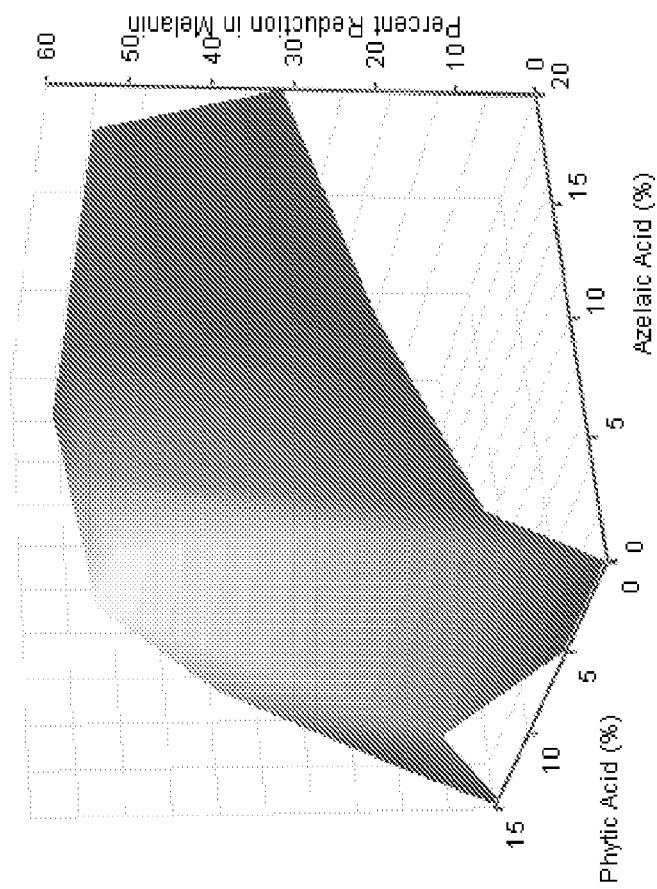
FIG. 1 is a surface plot of melanin reduction in cells incubated in the presence of varying concentrations of Azelaic acid and Phytic acid.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes are described as an order of individual steps or using specific materials, it is appreciated that described steps or materials may be interchangeable such that the description of the invention includes multiple parts or steps arranged in many ways as is readily appreciated by one of skill in the art. The materials used in a composition are illustrated by one or more activities of the materials. It is appreciated that these materials may have more than one activity. Each of these activities may or may not be listed herein, but are recognized by one of skill in the art.

The invention has utility as a composition suitable for reducing melanin content of the skin, and use of the composition for promoting lightening of the skin. Compositions are provided that include phytic acid and optionally azelaic acid or glycolic acid as active melanin reducing agents. It was surprisingly discovered that, contrary to the art recognized requirement of relatively high levels of these agents for skin lightening, that combining phytic acid with azelaic acid or a hydroxy acid at sub-clinically effective levels provides synergistic and improved skin lightening properties with greatly reduced irritation. Compositions are illustratively provided that include azelaic acid or one or more hydroxy acids at levels of 0.1% to 15% by weight, and phytic acid of 0.1% to 10% by weight to achieve greater and longer lasting skin lightening properties than azelaic acid at 20% or phytic acid at 10%.

The current primary therapeutic for treatment of hyperpigmentation is 1,4 benzenediol, known by the common name hydroquinone. While effective, hydroquinone therapies produce significant side effects of burning, redness, sensitization and irritation. The synergistic combination of phytic acid with azelaic acid, or a hydroxy acid, or both, with phytic acid at the relatively low concentrations of the inventive composition provides skin lightening properties similar to hydroquinone at prescription strength of 4%. The inventive compositions achieve improved skin lightening properties with fewer side effects of treatment.

A composition is provided that includes phytic acid and optionally azelaic acid, or one or more hydroxy acids, or both in the composition with phytic acid at concentrations that synergistically act to reduce melanin content in a subject or portion thereof The azelaic acid or a hydroxy acid is optionally present at 0.1 to 15 percent by weight and the phytic acid present at 0.1 to 8 percent by weight. In some embodiments, azelaic acid and phytic acid are present as the only skin lightening agents present in a composition. In some embodiments phytic acid and glycolic acid are present as the only skin lightening agents present in the composition. Other materials are optionally included in a composition such as emollients, thickeners, carriers, or vehicles, so as to form a liquid, gel, or cream suitable for topical application to the skin of a subject.

Azelaic acid is optionally present in a composition in amounts from 0.1% to 15% by weight or any value or range therebetween. In some embodiments, azelaic acid is present from 1.0% to 10% by weight. In some embodiments, azelaic acid is present from 1.0% to 5% by weight. Optionally, azelaic acid is present at 2.0% by weight. In some embodiments, the azelaic acid will be entirely in solution.

A hydroxy acid is optionally present in a composition in amounts from 0.1% to 15% by weight or any value or range therebetween. In some embodiments, hydroxy acid is present from 1.0% to 10% by weight. In some embodiments, hydroxy acid is present from 1.0% to 5% by weight. Optionally, hydroxy acid is present at 2.0% by weight. Glycolic acid is an exemplary hydroxy acid that is optionally present at any of the aforementioned levels or ranges of levels.

Some embodiments include both azelaic acid and a hydroxy acid, optionally glycolic acid, at amounts of 0.1 to 15 percent by weight each, optionally 1.0% to 10% by weight each, optionally 1.0% to 5% by weight each. Optionally, both azelaic acid and glycolic acid are present at 2% by weight.

Phytic acid is present in a composition at 0.1% and 10.0% by weight or any value or range therebetween. In some embodiments, phytic acid is present at 1.0% to 5.0% by weight. Optionally, phytic acid is present at 0.5% to 5% by weight. Optionally, phytic acid is present at 2.0% by weight.

A composition is optionally an aqueous composition defined herein as 40% or greater water. Water is optionally purified so as to remove contaminants such as solids and other microorganisms, or subjected to processes to remove contaminating ions. Illustratively, compositions include deionized water prepared by methods and using apparatuses known in the art. Methods of purifying or filtering water are well known in the art. It is appreciated that some embodiments of the composition are anhydrous.

A composition optionally includes one or more non-aqueous solvents such as an alcohol. Illustratively, a solvent is ethanol, isopropyl alcohol, methanol, ethoxydiglycol, benzyl alcohol, polyethylene glycol, dimethylisosorbide, triacetin (glyceryl triacetate), butylene glycol, propylene glycol, hexylene glycol, or other appropriate solvent as recognized in the art. In some embodiments, an alcohol is ethanol. Optionally, ethanol is specially denatured ethanol. An illustrative example of ethanol is SD alcohol 40-B. Alcohol is optionally present at 5% to 99.8% by weight, optionally 10% to 45% by weight. Optionally, alcohol is present at 20% to 30% by weight. In some embodiments, the composition is anhydrous.

A composition optionally includes one or more hydroxy acids. Examples of hydroxy acids illustratively include: beta-hydroxy acids illustratively salicylic acid, acetylsalicylic acid, among others; or alpha-hydroxy acids illustratively mandelic acid, glycolic acid, lactic acid, tartaric acid, malic acid, and citric acid, among others. Optionally, a composition includes mandelic acid as the sole hydroxy acid. A hydroxy acid is optionally preset at an amount of 0.1% to 20% by weight. Optionally, a hydroxy acid is present at from 1.0% to 10% by weight or any value or range therebetween. Optionally, a hydroxy acid is mandelic acid preset at from 1.0% to 5% by weight, optionally at 3.0% by weight. Optionally, a hydroxy acid is glycolic acid preset at from 1.0% to 5% by weight, optionally at 3.0% by weight. Optionally, both mandelic acid and glycolic acid are present. Optionally, glycolic acid is present absent mandelic acid. In some embodiments, one or more hydroxy acids are present and azelaic acid is absent.

A composition optionally includes one or more vitamins. A vitamin is illustratively vitamin A or its derivatives, vitamin C or its derivatives, vitamin E or its derivatives, vitamin D, vitamin K, vitamin 131, vitamin B2, vitamin B3, vitamin B5, vitamin B6, vitamin B8, vitamin B9, or vitamin B12. Optionally, a vitamin A derivative is retinal, retinoic acid, retinyl ester, retinol, tretinoin, isotretinoin, adapalene, tazarotene, or combinations thereof. Vitamin A or a derivative thereof is optionally present at between 0.001 to 5 weight percent. Vitamin C is optionally present as L-ascorbic acid. Vitamin C derivatives are optionally esters of ascorbic acid with fatty acids or their salts. An illustrative ester of ascorbic acid with fatty acids is ascorbyl palmitate. Vitamin C is optionally present at 0.1% to 35%. A vitamin is optionally vitamin B3 (niacinamide, niacin, or nicotinic acid). Vitamin B3 is optionally present at 1.0 to 10% by weight, optionally 1.0% to 5.0% by weight, optionally at 3.0% by weight. A vitamin is optionally niacinamide present at 1.0% to 5.0% by weight, optionally at 3.0% by weight. In some embodiments, a composition is free of all vitamins with the exception of niacinamide.

A composition optionally includes one or more additives. It is appreciated, however, that a composition is optionally free of an additive. An additive illustratively is one or more antioxidants, antiperspirants, anti-static agents, buffering agents, bulking agents, chelating agents, cleansers, colorants, conditioners, deodorants, diluents, dyes, emollients, flavonoids, fragrances, hair conditioners, humectants, ionization agents, moisturizers, occlusive agents, perfuming agents, pearlescent aids, perfuming agents, permeation enhancers, pH-adjusting agents, preservatives, protectants, skin penetration enhancers, softeners, solubilizers, sunscreens, sun blocking agents, sunless tanning agents, or viscosity modifiers. Optionally, a composition is free of 1,2-decanediol. The source and type of additive operable herein is readily understood by one of skill in the art.

A humectant is optionally included in a composition. Illustrative examples of humectants include glycerin, glycereth-7 trimethyl ether, propylene glycol and propylene glycol derivatives, guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, salts of hyaluronic acid, lactamide monoethanolamine, acetamide monoethanolamine and derivatives, esters, salts and mixtures thereof, as well as any suitable humectant found in Handbook of Pharmaceutical Additives published by Gower where one of ordinary skill in the art will recognize suitable humectants contained therein. A humectant, when present, is optionally present at 1.0% to 15% by weight, optionally at 5.0% to 10% by weight. In some embodiments, a humectant is glycereth-7 trimethyl ether present at 5% to 10% by weight, optionally 7.0% by weight.

A composition optionally includes a pH-adjusting agent. Illustratively, a pH adjusting agent is triethanolamine. Triethanolamine associates with one or more acids present in the composition forming salts. The salts are less irritating than the free acids. The presence of triethanolamine in the composition also serves to raise the pH to a more topically acceptable level. It is appreciated that other pH-adjusting agents suitable to increase the pH relative to a composition without a pH-adjusting agent are operable in a composition. Such pH-adjusting agents are known in the art.

Some embodiments of a composition include one or more anti-irritants. Illustrative examples of anti-irritants include materials derived from plants such as plant extracts or plant juices. An anti-irritant is optionally a plant extract, illustratively, *Anthemis nobilis* flower extract, bisabolol, alpha-bisabolol, *Arctium lappa*, *Boerhavia diffusa* root extract, *Echinacea*, among other plant extracts known in the art. Other examples of an anti-irritant include calcium gluconate, coenzyme Q10, among others known in the art. An anti-irritant is optionally present in a composition at from 0.001% to 2.0% by weight.

A composition is optionally provided as a serum, lotion, cream, gel, bar, ointment, in pad form, or other desirable form for topical administration to a subject. Optionally, the composition is supplied in the form of an aqueous solution. Compositions according to the invention optionally have a pH in the range between 2.0 and 6.0 or any value or range therebetween. A pH of the composition is optionally from 3.0 to 4.5, optionally 3.0 to 4.0, optionally 3.5 to 4.5, optionally 3.5 to 4.0.

Also provided are processes of reducing melanin levels in a subject or portion thereof, optionally in the skin of a subject. A process includes administering a therapeutically effective amount of a composition as described herein, and equivalents thereof, to the skin of a subject, or to a cell, and reducing the level of melanin in the skin or cell by the administering. A therapeutically effective amount is that sufficient to reduce the level of melanin on the tissue onto which the composition is applied.

A composition is optionally administered to a subject by contact administration, illustratively, topical administration. A subject is optionally a patient. A subject is optionally a mammal such as a human, non-human primate, equine, goat, bovine, sheep, pig, dog, cat, or rodent. A subject is optionally a cell, or collection of cells illustratively in the form of a tissue or culture of cells.

A composition is administered to a subject once or more daily until the desired level of melanin decrease is achieved. A composition is optionally administered 1, 2, 3, 4, 5 or more times daily. Administration is optionally 1, 2, 3, 4, 5, 6, 7, or more times per week. Administration is optionally continued until a desired amount of melanin decrease is achieved. A composition is optionally administered once. A composition is optionally administered for 1, 2, 3, 4, 5, 6, 7, 8, 9, 10, 11, 12, or more weeks.

A composition is optionally administered to a subject and allowed to incubate in contact with the subject for a desired incubation time followed by removal such as by washing or wiping with a cloth. A composition is optionally incubated on the skin for 1, 2, 3, 4, 5, 6, 7, 8, 9, 10 or more minutes. In some embodiments, a composition is allowed to remain in contact with the subject indefinitely without conscious or intentional removal.

Various aspects of the present invention are illustrated by the following non-limiting examples. The examples are for illustrative purposes and are not a limitation on any practice of the present invention. It will be understood that variations and modifications can be made without departing from the spirit and scope of the invention.

EXAMPLE 1

Compositions are formed with the materials at levels illustrated in Table 1:

TABLE 1

| Ingredient (INCI name) | % w/w | Brand name | Supplier |
|---|---|---|---|
| Water | q.s. to 100 | | |
| Mandelic acid | 3.00 | DL-Mandelic Acid | Spectrum |
| Phytic acid, 50% | 0.01 to 8.0 | Phytic Acid Extreme | Biosil Technologies, Inc. |
| Niacinamide | 3.00 | Niacinamide PC | DSM Nutritional Products, Inc. |
| Triethanolamine | 2.30 | Trolamine NF | Ineos Oxide (Univar) |
| SD Alcohol 40B, 200 proof | 24.30 | | Pharmco |
| Glycereth-7 trimethyl ether | 7.00 | Coscap G7-MC | Phoenix Chemical |
| PEG-8/SMDI Copolymer | 3.00 | Polyolprepolymer -15 | Barnet |
| Azelaic acid, 98% | 0.1 to 15.0 | | Penta International |
| Bisabolol | 0.20 | Dragosantol 100 | Symrise |

Compositions are formulated by varying the amount of either azelaic acid, phytic acid, or both by varying the amount of water accordingly. Formulas A-Z are illustrated in Table 2. All other ingredients remain as in Table 1.

TABLE 2

| Formula | Phytic Acid, 50% (% w/w) | Azelaic acid (% w/w) |
|---|---|---|
| A | 0.50 | 2.00 |
| B | 1.00 | 2.00 |
| C | 2.00 | 2.00 |
| D | 5.00 | 2.00 |
| E | 10.00 | 2.00 |
| F | 15.00 | 2.00 |
| G | 2.00 | 0.50 |
| H | 2.00 | 5.00 |
| I | 2.00 | 10.00 |

TABLE 2-continued

| Formula | Phytic Acid, 50% (% w/w) | Azelaic acid (% w/w) |
|---|---|---|
| J | 2.00 | 15.00 |
| K | 2.00 | 20.00 |
| L | 5.00 | 10.00 |
| M | 0.00 | 1.00 |
| N | 0.00 | 2.00 |
| O | 0.00 | 3.00 |
| P | 0.00 | 4.00 |
| Q | 0.00 | 5.00 |
| R | 0.00 | 10.00 |
| S | 0.00 | 20.00 |
| T | 1.00 | 0.00 |
| U | 2.00 | 0.00 |
| V | 3.00 | 0.00 |
| W | 4.00 | 0.00 |
| X | 5.00 | 0.00 |
| Y | 10.00 | 0.00 |
| Z | 15.00 | 0.00 |

Compositions of Table 1 including specific Formulas A-Z are made by the combination of two phases. Phase 1 is formed by adding mandelic acid, phytic acid, niacinamide and triethanolamine to water with gentle mixing. Phase 2 is formed by adding glycereth-7 trimethyl ether, PEG-8/SMDI copolymer, azelaic acid, and bisabolol to SD alcohol 40-B with gentle mixing. Phase 1 and Phase 2 are then combined by slow addition of Phase 1 to Phase 2 with continuous, non-vortex propeller mixing until a homogeneous composition is formed. The compositions are then stored from light in sealed containers.

EXAMPLE 2

Compositions are formed with the materials at levels illustrated in Table 3:

TABLE 3

| Ingredient (INCI name) | % w/w | Brand name | Supplier |
|---|---|---|---|
| Water | q.s. to 100 | | |
| Mandelic acid | 3.00 | DL-Mandelic Acid | Spectrum |
| Phytic acid, 50% | 0.01 to 8.0 | Phytic Acid Extreme | Biosil Technologies, Inc. |
| Niacinamide | 3.00 | Niacinamide PC | DSM Nutritional Products, Inc. |
| Triethanolamine | 2.30 | Trolamine NF | Ineos Oxide (Univar) |
| SD Alcohol 40B, 200 proof | 24.30 | | Pharmco |
| Glycereth-7 trimethyl ether | 7.00 | Coscap G7-MC | Phoenix Chemical |
| PEG-8/SMDI Copolymer | 3.00 | Polyolprepolymer-15 | Barnet |
| Glycolic acid | 0.1 to 15.0 | | Sigma-Aldrich |
| Bisabolol | 0.20 | Dragosantol 100 | Symrise |

Compositions are formulated by varying the amount of either glycolic acid, phytic acid, or both by varying the amount of water accordingly. Formulas AA-OO are illustrated in Table 4. All other ingredients remain as in Table 3.

TABLE 4

| Formula | Phytic Acids 50% (% w/w) | Glycolic acid (% w/w) |
|---|---|---|
| AA | 0.50 | 2.00 |
| BB | 1.00 | 2.00 |
| CC | 2.00 | 2.00 |
| DD | 4.00 | 2.00 |
| EE | 6.00 | 2.00 |
| FF | 8.00 | 2.00 |
| GG | 2.00 | 0.50 |
| HH | 2.00 | 1.00 |
| II | 2.00 | 4.00 |
| JJ | 2.00 | 8.00 |
| KK | 2.00 | 15.00 |
| LL | 0.00 | 2.00 |
| MM | 0.00 | 20.00 |
| NN | 2.00 | 0.00 |
| OO | 10.00 | 0.00 |

EXAMPLE 3

The ability of the compositions of Examples 1 and 2 are tested for their ability to reduce melanin levels in vitro and compared to standard compositions that contain as a replacement for phytic acid, azelaic acid, and glycolic acid, hydroquinone at either the OTC concentration of 2% or the prescription concentration of 4%. In addition, standard compositions M-Z and LL-OO are formed and used as controls.

The in vitro assay used is the MELANODERM skin model available from MatTek Corp., Ashland, Mass. This assay is essentially as described by Majmudar, G., et al., J. Cosmet. Sci., 361-367, (1998). The melanoderm assay is performed using normal, human-derived epidermal keratinocytes and melanocytes that are cultured to form a multilayered, highly differentiated model of the human epidermis. The culture of cells forms a layer that is suitable for topical administration of test compositions to determine either the prevention of melanin production and pigmentation, or the reduction of pre-established melanin and reduction of pigmentation.

Cultured cells are grown as per the manufacturer's instructions for 10 or 14 days either in the presence of 25 μl of test samples of compositions at indicated concentrations or in the presence of 25 μl of control sample. The samples are applied to the surface of the cultured cells in the plate wells. To assay for the level of melanin, the tissue in each well is homogenized in 0.45 ml of 1% SDS containing 0.05 mM EDTA, and 10 mM Tris HCl, pH 6.8. Proteinase K (5 mg/ml; 20 μl) is added to the homogenate and incubated overnight at 45° C. An additional 20 μl aliquot of Proteinase K is added and incubation continued for an additional 4 hr. The homogenate is made basic by adding 50 μl of 500 mM sodium carbonate, and 10 μl of 30% hydrogen peroxide is added. Samples are maintained at 80° C. for 30 minutes and cooled. The mixture is extracted with 100 p1 of Chloroform: Methanol (2:1). After centrifugation at 10,000× g for 10 min, the optical density at 405 nm is determined. Synthetic melanin (Sigma-Aldrich, St. Louis Mo.) is subjected to the same procedure for construction of a standard curve.

The compositions of Formulas A-L or AA-KK, hydroquinone controls, and other controls some containing no azelaic acid, phytic acid, or glycolic acid, or none of all three, are applied each to individual cultures of cells as described above. The level of melanin present in the cells is determined by oxidatively degrading melanin in the cell samples into soluble byproducts by heating it in dilute, alkaline $H_2O_2$ and measuring the fluorescence of the resulting solution using a Horiba Fluor° Max spectrofluorometer. The results of several formulations are illustrated in Table 4.

TABLE 4

| Treatment | Melanin Content (μg/tissue sample) | |
|---|---|---|
| | Day 10 | Day 14 |
| Water control | 20.3 | 36.1 |
| Hydroquinone 2% | 10.8 | 17.7 |
| Hydroquinone 4% | 8.1 | 10.5 |
| M | 18.0 | 33.1 |
| N | 17.6 | 31.8 |
| O | 17.1 | 30.5 |
| P | 16.8 | 29.3 |
| Q | 16.0 | 28.9 |
| R | 15.6 | 28.2 |
| S | 13.9 | 24.4 |
| T | 21.7 | 36.7 |
| U | 21.5 | 36.3 |
| V | 20.9 | 35.7 |
| W | 20.2 | 34.3 |
| X | 19.4 | 33.5 |
| Y | 18.1 | 32.7 |
| Z | 20.6 | 36.3 |
| B | 14.3 | 16.7 |
| C | 9.4 | 11 |
| D | 9.1 | 10.8 |
| E | 12.5 | 15.1 |
| F | 17.7 | 22.1 |
| H | 8.7 | 10.1 |
| I | 8.6 | 10.4 |
| J | 8.9 | 10.7 |
| K | 9.4 | 12.1 |
| L | 8.3 | 10.1 |

Azelaic acid at concentrations of 1, 2%, 3%, 4%, 5%, 10% and 20%, when used in formulations in the absence of phytic acid, has modest efficacy compared with the hydroquinone standards. Compositions that include phytic acid at up to 15% in the absence of azelaic acid are less effective. However, the combination of azelaic acid and phytic acid at sub efficacious levels of each shows melanin reductions that approximate that achieved with the prescription strength hydroquinone (4%). FIG. 1 illustrates a surface graph of the percent reduction in melanin levels calculated from the data presented in Table 4 at day 10 at various combinations of azelaic acid and phytic acid. It can be seen that in the presence of either azelaic acid or phytic acid alone, small levels of melanin reduction are observed. Similar results are observed at day 14. Interestingly, phytic acid alone shows little efficacy at all concentrations tested. When both azelaic acid and phytic acid are combined at sub efficacious does of each, a dramatic and synergistic increase in melanin reduction is observed, with the greatest synergy observed between 1% and 5% of each.

FIG. 2A illustrates the synergistic ability to reduce melanin levels of compositions including phytic acid levels at a constant, sub-clinical dose of azelaic acid at day 10. The additive (light bars) represents the expected additive level of azelaic acid with phytic acid at the indicated concentrations from the results of Table 4. The combined result (dark bars) illustrates surprisingly synergistic observed results that are far superior that that expected from simple additive effect. This synergistic improvement is reduced, but still present at 10% phytic acid and is substantially additive at high levels, e.g. 15%, of phytic acid. These results combined with the results in FIG. 1 indicate a synergistic relationship in melanin reduction between 1% and approximately 5% of phytic acid at 2% azelaic acid.

FIG. 2B illustrates the synergistic ability to reduce melanin levels of compositions including a constant 2% amount of phytic acid and varying azelaic acid at sub-clinical doses. The additive (light bars) represents the expected additive level of azelaic acid with phytic acid at the indicated concentrations. The combined result (dark bars) illustrates the synergistically, and surprisingly far superior observed results than that expected from simple additive effect. This synergistic improvement is reduced, at increasing concentrations of azelaic acid but remains significantly synergistic at concentrations out to 20% azelaic acid. These results combined with the results in FIG. 1 indicate a synergistic relationship in melanin reduction of azelaic acid at 2% phytic acid, with the greatest synergy observed between 1% and approximately 5%.

Figure 3:
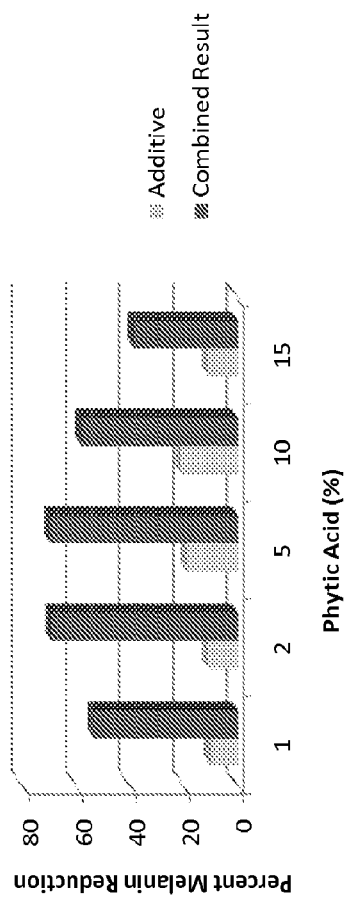
FIG. 3 represents the synergistic combination of Azelaic acid and Phytic acid at either (A) 2% Azelaic acid or (B) 2% Phytic acid illustrating much greater than additive affect of the combination of the two agents at day 14, particularly at sub-clinical doses of each.
Figure 3:
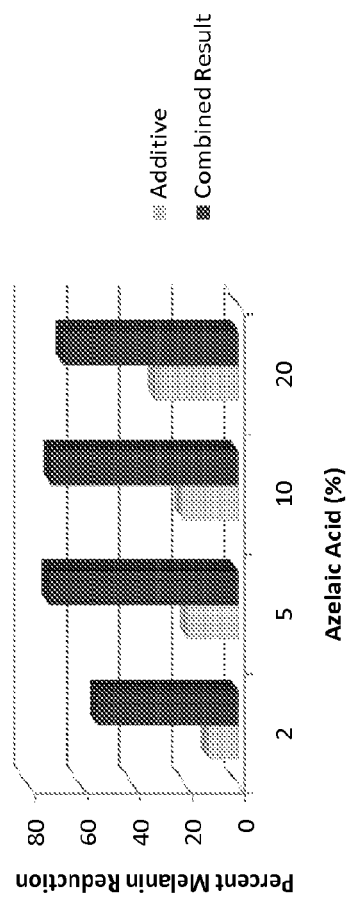

Similar results are found at day 14 for both azelaic acid and phytic acid (FIG. 3 A, B). Also, similar efficacy of compositions of Table 3 and formulas S-CC are also observed.

Similar results of synergistic reductions of melanin formation are observed with the other compositions of Tables 2 and 4.

Figure 2:
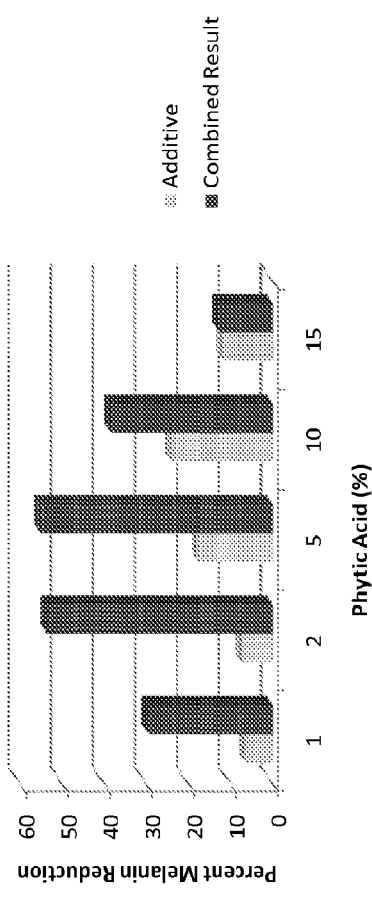
FIG. 2 represents the synergistic combination of Azelaic acid and Phytic acid at either (A) 2% Azelaic acid or (B) 2% Phytic acid illustrating much greater than additive affect of the combination of the two agents at day 10, particularly at sub-clinical doses of each.
Figure 2:
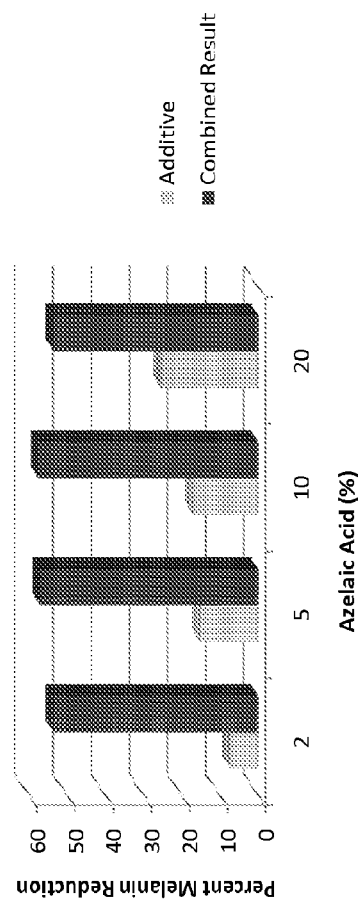

FIGS. 1-3 collectively demonstrate a synergistic relationship between azelaic acid and phytic acid at low concentrations of each.

EXAMPLE 3

The ability of the compositions of Formulas A-L or AA-KK are tested in vivo using human subjects in clinical studies substantially as described in U.S. Pat. No. 6,057,360. Visible hyperpigmentation in the skin of subjects is clinically evaluated using a 0 (none) to 3 (dark) clinical rating scale. Subjects are tested that are self described as having either Caucasian or black skin. Several forms of hyperpigmentation are reported in the test subjects including age spots, sun spots, or post-inflammatory and related hyperpigmentation. Each hyperpigmentation spot in a standard sample area is rated on the 0-3 scale, with the sum of the ratings recorded for each sample area. Subjects apply test compositions of one of formulas A-L, AA-KK, or control twice a day for period ranging from 12 weeks to 24 weeks without knowledge of which formulation or control they are applying. As a control, a 2% hydroquinone cream, water, or compositions of any of Formulas M-ZZ or LL-OO are used. Hyperpigmentation is scored by a blinded investigator at baseline and at each evaluation period. Alternatively, the level of melanin content is measured by spectrophotometry as described by Dwyer, T, et al., $Cancer$ $Epidemiol$ $Biomarkers$ $Prev$, 1998; 7; 203-206.

The compositions of formulations A-L and AA-KK each demonstrate greater improvement (reduction) in hyperpigmentation than is observed in either water control or 2% hydroquinone controls. Test formulations A-L demonstrate greater hyperpigmentation reduction relative to control formulas M-ZZ. Test formulations AA-KK also demonstrate greater hyperpigmentation reduction relative to control formulas MM-OO.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition for promoting a reduction in skin pigmentation comprising:
   azelaic acid at 0.1 to 1.5 percent by weight, azelaic acid is alone or in combination with one or more hydroxy acids; and
   phytic acid present at 0.1 to 8 percent by weight;
   wherein said azelaic acid and said phytic acid are present in synergistic concentrations to reduce melanin levels in a melanin containing cell when contacted to said cell.

2. The composition of claim 1 comprising both azelaic acid and one or more hydroxy acids.

3. The composition of claim 1 wherein said composition is anhydrous.

4. The composition of claim 1 wherein at least one of said hydroxy acids is an alpha hydroxy acid.

5. The composition of claim 1 wherein said hydroxy acid is glycolic acid, mandelic acid, or combinations thereof.

6. The composition of claim 1 wherein said azelaic acid is present at 1.0 to 10 percent by weight.

7. The composition of claim 1 wherein said azelaic acid is present at 1.0 percent to 5.0 percent by weight.

8. The composition of claim 1 wherein said phytic acid is present at 1.0 percent to 5.0 percent by weight.

9. The composition of claim 1 wherein said azelaic acid and said phytic acid are each present at from 0.5 percent to 5 percent by weight.

10. The composition of claim 1 further comprising one or more vitamins.

11. The composition of claim 10 wherein said vitamin is niacinamide.

12. A process of reducing melanin content in a cell comprising
    contacting a cell with a composition comprising
    azelaic acid present at 0.1 to 15 percent by weight; and
    phytic acid present at 0.1 to 10 percent by weight;
    said azelaic acid and phytic acid present in synergistic concentrations to reduce melanin content in said cell, and
    reducing melanin content in said cell by said step of contacting.

13. The process of claim 12 wherein said azelaic acid is present at 1.0 to 10 percent by weight.

14. The process of claim 12 wherein said azelaic acid is present at 1.0 percent to 5 percent by weight.

15. The process of claim 12 wherein said phytic acid is present at 1.0 percent to 5 percent by weight.

16. The process of claim 12 wherein said azelaic acid and said phytic acid are each present at from 1.0 percent to 5% by weight.

17. The process of claim 12 wherein said composition further comprises one or more hydroxy acids.

18. The process of claim 17 wherein said hydroxy acid is mandelic acid, glycolic acid, or combinations thereof.

* * * * *